United States Patent
Basset et al.

(10) Patent No.: US 10,308,572 B2
(45) Date of Patent: Jun. 4, 2019

(54) PROCESS FOR COMPOUND TRANSFORMATION

(71) Applicant: King Abdullah University of Science and Technology, Thuwal (SA)

(72) Inventors: Jean-Marie Maurice Basset, Thuwal (SA); Emmanuel Callens, Thuwal (SA); Nassima Riache, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 0 days.

(21) Appl. No.: 15/739,044

(22) PCT Filed: Jun. 23, 2016

(86) PCT No.: PCT/IB2016/053758
§ 371 (c)(1),
(2) Date: Dec. 21, 2017

(87) PCT Pub. No.: WO2016/207835
PCT Pub. Date: Dec. 29, 2016

(65) Prior Publication Data
US 2018/0179126 A1     Jun. 28, 2018

Related U.S. Application Data

(60) Provisional application No. 62/184,377, filed on Jun. 25, 2015.

(51) Int. Cl.
*C07C 6/04* (2006.01)
*C07C 6/10* (2006.01)
(Continued)

(52) U.S. Cl.
CPC ............ *C07C 6/10* (2013.01); *C07C 6/04* (2013.01); *C07C 67/475* (2013.01);
(Continued)

(58) Field of Classification Search
CPC ............ C07C 6/10; C07C 6/04; C07C 67/475; C07C 29/205
(Continued)

(56) References Cited

U.S. PATENT DOCUMENTS 6,469,225 B1   10/2002   Basset et al.
7,638,672 B2 *  12/2009   Coperet ............... C07C 6/04
                                                585/643
(Continued)

FOREIGN PATENT DOCUMENTS

EP    0191675 A1   8/1986
EP    0259215 A1   3/1998
(Continued)

OTHER PUBLICATIONS

Bouchra et al: "A Well-Defined, Silica-Supported Tungsten Imido Alkylidene Olefin Metathesis Catalyst", Organometallics, vol. 25, No. 15, Jul. 2006 (Jul. 2006), pp. 3554-35573 (Year: 2006).*

(Continued)

*Primary Examiner* — Deborah D Carr
(74) *Attorney, Agent, or Firm* — Billion & Armitage; Benjamin C. Armitage

(57) ABSTRACT

Embodiments of the present disclosure provide for methods of using a catalytic system to chemically transform a compound (e.g., a hydrocarbon). In an embodiment, the method does not employ grafting the catalyst prior to catalysis. In particular, embodiments of the present disclosure provide for a process of hydrocarbon (e.g., C1 to C20 hydrocarbon) metathesis (e.g., alkane, olefin, or alkyne metathesis) transformation, where the process can be conducted without employing grafting prior to catalysis.

19 Claims, 10 Drawing Sheets

Previous work

Single catalytic mutlifunctional heterogenous system: W grafted on silica

Dual catalytic system: de/hydrogenation catalyst (Ir) and olefinmetathesis catalyst (W and Mo in homogeneous phase or supported Re₂O₇ on Al₂O₃)

This discovery

W, Mo, Cr, Ta, Re molecular solution (with or without additives) or their mixture in heterogeneous system by simple Impregnation Protocol

(51) Int. Cl.
  C07C 9/14    (2006.01)
  C10L 1/06    (2006.01)
  C07C 11/02   (2006.01)
  C07C 13/02   (2006.01)
  C10G 29/20   (2006.01)
  C07C 67/475  (2006.01)
  C07C 69/593  (2006.01)

(52) U.S. Cl.
  CPC ............. *C10G 29/205* (2013.01); *C10L 1/06* (2013.01); *C07C 2521/08* (2013.01); *C07C 2531/12* (2013.01); *C07C 2531/22* (2013.01); *C10G 2400/02* (2013.01)

(58) Field of Classification Search
  USPC ........................................................ 554/124
  See application file for complete search history.

(56) References Cited

U.S. PATENT DOCUMENTS

| 2011/0245570 A1 | 10/2011 | Nicholas et al. |
| 2012/0316057 A1* | 12/2012 | Taoufik ................... C07F 11/00 502/155 |

FOREIGN PATENT DOCUMENTS

| EP | 2022772 A1 | 2/2009 |
| FR | 2736646 A1 | 11/1997 |
| FR | 2840607 A1 | 12/2003 |
| FR | 2841240 A1 | 12/2003 |
| FR | 2841241 A1 | 12/2003 |
| FR | 2852866 A1 | 10/2004 |
| FR | 2872510 A1 | 1/2006 |
| WO | 1994000426 A1 | 1/1994 |
| WO | 1998002244 A1 | 1/1998 |
| WO | 2000027781 A1 | 5/2000 |
| WO | 2001004077 A1 | 1/2001 |
| WO | 200207110 A2 | 1/2002 |
| WO | 2002022262 A2 | 3/2002 |
| WO | 2003061823 A1 | 7/2003 |
| WO | 2003066552 A1 | 8/2003 |
| WO | 2000027781 A1 | 5/2005 |
| WO | 2008001040 A1 | 1/2008 |
| WO | 2008075031 A1 | 6/2008 |
| WO | 2008152371 A1 | 12/2008 |
| WO | 2009044107 A1 | 4/2009 |
| WO | 2009115805 A1 | 9/2009 |
| WO | 2015079321 | 6/2015 |

OTHER PUBLICATIONS

Jaehong et al: "Mesoporous silica-supported catalysts for metathesis: application to a circulating flow reactor", Chemical Communications—Chemcom., vol. 46, No. 5, Jan. 2010 (Jan. 2010), pp. 806-808. (Year: 2010).*
Le Roux et al: "Detailed Structural Investigation of the Grafting of [Ta(=CHtBu)CH2tBu)3] and [Cp*TaMe4] on Silica Partially Dehydroxylated at 700° C and the Activity of the Grafted Complexes toward Alkane Metathesis", vol. 126, No. 23, Sep. 2004, p. 13391-99. (Year: 2004).*
John Smith et al: "Organometallic Complexes of Molybdenum and Tungsten as Catalyst Pre-cursors in the Disproportionation of Propene", Journal of the Chemical Society, Dalton Transactions (Inorganic Chemistry), No. 16, Jan. 1974, p. 1742-47 (Year: 1974).*
Search Report and Written Opinion for PCT/IB2016/053758 dated Sep. 21, 2016.
Rhers et al., "A Well-Defined, Sili-Supported Tungsten Imido Alkylidene Olefin Metathesis Catalyst", Organometallics, vol. 25, No. 15, Jul. 2006, pp. 3554-3557.
Le Roux, et al., "Detailed Structural Investigation of the Grafting of [Ta(=CHtBu) (CH2tBu)3] and [Cp*TaMe4] on Silica Partially Dehyroxylated at 700 C and the Actiity of the Grafted Complexes toward Alkane Metathesis", Journal of the American Chemical Society, vol. 126, No. 41, Sep. 23, 2004, pp. 13391-13399.
Lim, et al., "Mesoporous silica-supported catalysts for metathesis: appliation to a circulating flow reactor", Chemical Communications—Chemco., vol. 46, No. 5, Jan. 2010, pp. 806-808.
Smith, et al., "Organometallic Complexes of Molybdenum and Tungsten as Catalyst of Molybdenum and Tungsten as Catalyst Pre-cursors in the Disproportionation of Propene", Journal of the Chemical Society, Dalton Transaction (Inorganic Chemistry), No. 16, Jan. 1974, pp. 1742-1747.
Callens, et al., "Simpl addition of silica to an alkane solution of a Wilkinson WMe6 or Schrock W alkylidyne complex gives an active complex for saturated and unsaturated hydrocarbon metathesis", Chemical Communication, 2015, 51, pp. 15300-15303.
Michael C Haibach et al., "Alkane Metathesis by Tandem Alkane-Dehydrogenation-Olefin-Metathesis Catalysis and Related Chemistry," Accounts of chemical research, 2012, 947-958.
Robert L. Burnett et al., "Mechanism and Poisoning of the Molecular Redistribution Reaction of Alkanes with a Dual-Functional Catalyst System," Journal of Catalysis, 1973, 55-64.
Jean-Marie Basset et al., "Metathesis of Alkanes and Related Reactions," Accounts of chemical research, Feb. 2010, 323-334.
Christophe Coperet, "C—H Bond Activation and Organometallic Intermediates on Isolated Metal Centers on Oxide Surfaces," Chem. Rev., 2010, 656-680.
Alan S. Goldman et al., "Catalytic Alkane Metathesis by Tandem Alkane Dehydrogenation-Olefin Metathesis," Science, Apr. 14, 2006, 257-262.
Manoja K. Samantaray et al., "WMe6 Tamed by Silica: ≡Si—O—WMe5 as an Efficient, Well-Defined Species for Alkane Metathesis, Leading to the Observation of a Supported W-Methyl/Methylidyne Species," JACS, 2014, 1054-1061.
Riache N. et al., "Striking difference between alkane and olefin metathesis using the well-defined precursor [ṄSi—O—WMe5]: indirect evidence in favour of a bifunctional catalyst W alkylidene-hydride," Catalysis Science & Technology, Royal Society of Chemistry, 2015, 280-285.
Nassima Riache et al., Cyclooctane Metathesis Catalyzed by Silica-Supported Tungsten Pentamethyl [(SiO)W(Me)5]: Distribution of Macrocyclic Alkanes, Chemistry A European Journal Full Paper, 2014, 15089-15094.
Lourdes H. Pia. et al., "Dimers that Contain Unbridged W(IV)/W(IV) Double Bonds," Organometallics, 2006, 1978-1986.
Nassima Riache et al., "Silica-Supported Tungsten Carbynes (≡SiO)xW(≡CH)(Me)y (x=1, y=2; x=2, y=1): New Efficient Catalysts for Alkyne Cyclotrimerization," ACS Publications, 2015, 690-695.
Richard R. Schrock et al., "High-Oxidation-State Molybdenum and Tungsten Alkylidyne Complexes," American Chemical Society, 1986, 342-348.
Anthony J. Shortland et al. "Preparation and Properties of Hexamethyltungsten," J.C.S. Dalton, 1972, 872-876.
Laurel A. Morton et al., "Reactions of d0 tungsten alkylidyne complexes with O2 or H2O. Formation of an oxo siloxy complex through unusual silyl migrations," ChemComm, RSC Publishing, 2013, 9555-9557.
Callens E. et al., "Direct observation of supported W bis-methylidene from supported W-methyl/methylidyne species," ChemComm, The Royal Society of Chemistry, 2014, 3982-3985.
Erwan Le. Roux et al., "Well-Defined Surface Tungstenocarbyne Complexes through the Reaction of [W(=CtBu) (CH2tBu)3] with Silica," Organometallics, 2005, 4274-4279.
Jeffrey H. Wengrovius et al., "Metathesis of Acetylenes by Tungsten(VI)-Alkylidyne Complexes," American Chemical Society, 1981, 3932-3934.
Richard R. Schrock et al. "The Alkoxide Ligand in Olefin and Acetylene Metathesis Reactions," Pergamon, 1995, 3177-3195.
Erwan Le. Roux et al., "Silica-Alumina-Supported, Tungsten-Based Heterogeneous Alkane Metathesis Catalyst: Is it Closer to a Silica- or an Alumina-Supported System?," Wiley InterScience, 2007, 231-237.

(56) References Cited

OTHER PUBLICATIONS

Jérôme Joubert et al., "Alkane metathesis by a tungsten carbyne complex grafted on gamma alumina: Is there a direct chemical role of the support?," ScienceDirect, Journal of Catalysis, 2007, 507-513.
Jean-Marie Basset et al., "Surface Organometallic Chemistry: Molecular Approaches to Surface Catalysis," NATO ASI Series, Oct. 1987, 1-340.
Laurel A. Morton et al., "Tungsten Alkyl Alkylidyne and Bis-alkylidene Complexes. Preparation and Kinetic and Thermodynamic Studies of Their Unusual Exchanges," Organometallics, 2006, 427-434.
Laurel A. Morton et al., "Preparation of Tungsten Alkyl Alkylidene Alkylidyne Complexes and Kinetic Studies of Their Formation," JACS Article, American Chemical Society, 2007, 7277-7283.
Alois Furstner, "Alkyne Metathesis on the Rise," Angewandte Chemie International Edition, 2013, 2794-2819.
Wei Zhang et al., "Alkyne Metathesis: Catalysts and Synthetic Applications," Wiley Inter Science, 2007, 93-120.
Boris Van. Berlo et al., "Silica Immobilized Second Generation Hoveyda-Grubbs: A Convenient, Recyclable and Storageable Heterogeneous Solid Catalyst," Adv. Synth. Catal., 2008, 1949-1953.
Miriam Bru et al., "Ruthenium Carbenes Supported on Mesoporous Silicas as Highly Active and Selective Hybrid Catalysts for Olefin Metathesis Reactions under Continuous Flow," Chemistry A European Journal, 2013, 11661-11671.

\* cited by examiner

PROCESS FOR COMPOUND TRANSFORMATION

CROSS-REFERENCE TO RELATED APPLICATIONS

This application is a National Stage Application of PCT/IB2016/053758, filed on Jun. 23, 2016, which claims the benefit of and priority to U.S. Provisional Application Ser. No. 62/184,377, having the title "PROCESS FOR COMPOUND TRANSFORMATION," filed on Jun. 25, 2015, the disclosure of which is incorporated herein in by reference in its entirety.

BACKGROUND

Conversion of linear or cyclic alkanes to higher and lower homologs, namely alkane metathesis, is a promising valuable transformation in petrochemical and chemical industry (*Accounts Chem Res*, 2012, 45, 947-958). Disproportionation of hydrocarbons was initially discovered employing two supported heterogeneous catalytic systems operating at high temperature (*J Catal*, 1973, 31, 55-64). Later, it was found that silica supported tantalum mono and polyhydrides as well as polyalkyls and silica supported group VI polyhydrides polyalkyls, prepared by surface organometallic chemistry are efficient multifunctional single metal pre-catalysts for propane and higher alkane metathesis (*Chem Rev*, 2010, 110, 656-680). Variation of these formulations have been disclosed.

However, there is a need to find an easier and as or more efficient technique.

SUMMARY

Embodiments of the present disclosure provide for methods of using a catalytic system to chemically transform a compound (e.g., a hydrocarbon). In an embodiment, the method does not employ grafting the catalyst prior to catalysis. In particular, embodiments of the present disclosure provide for a process of hydrocarbon (e.g., C1 to C20 hydrocarbon) metathesis (e.g., alkane, olefin, or alkyne metathesis) transformation, where the process can be conducted without employing grafting prior to catalysis.

An embodiment of the present disclosure includes, among others, a method of chemical transformation (e.g., hydrocarbon metathesis) that includes: mixing an organometallic compound and a metal oxide in the presence of a hydrocarbon or a hydrocarbon mixture; and heating the mixture to about 25° C. to 200° C. for a time frame of about 1 day to 1 month to accomplish the transformation of the compound.

In an embodiment, the hydrocarbon can be selected from a saturated hydrocarbon, a unsaturated fatty acid ester, an olefin, a functionalized olefin, and a combination thereof. In an embodiment, the hydrocarbon can be selected from a C1-C20 alkane, a C2-C20 alkene, a C2-C20 alkyne, and a combination thereof, wherein each hydrocarbon is linear, branched, cyclic, and/or aromatic. In an embodiment, the hydrocarbon can be selected from: ethylene, n-butane, isobutane, butene, decane, cyclooctane, cyclododecane, hexane, pentanes $C_6$-$C_{30}$ hydrocarbons, 1-decene, 1-decyne, and a combination thereof.

In an embodiment, the metal in the organometallic compound is a transition metal (e.g., Ti, Zr, Hf, Ta, Nb, V, Cr, Mo, W, Re, and their mixtures) or mixture thereof. In an embodiment, the organometallic compound can be selected from: Wilkinson $d^0$ $WMe_6$ or Schrock type $d^0$ W metal alkylidyne complex or the organometallic compound can contain a chloride or an aryl oxide is associated with an alkylating agent (e.g., MeLi, $Me_2Zn$).

In an embodiment, the metal oxide can be selected from: silica, silica-alumina, γ-alumina, mesoporous silica, zeolite, metal organic frameworks (MOF), organic-inorganic mixed oxides, carbon black, carbon nanotubes, and a combination thereof.

Other methods, compositions, features, and advantages will be or become apparent to one with skill in the art upon examination of the following drawings and detailed description. It is intended that all such additional methods compositions, features and advantages be included within this description, be within the scope of the present disclosure, and be protected by the accompanying claims.

BRIEF DESCRIPTION OF THE DRAWINGS

Further aspects of the present disclosure will be more readily appreciated upon review of the detailed description of its various embodiments, described below, when taken in conjunction with the accompanying drawings.

DETAILED DESCRIPTION

Figure 1:
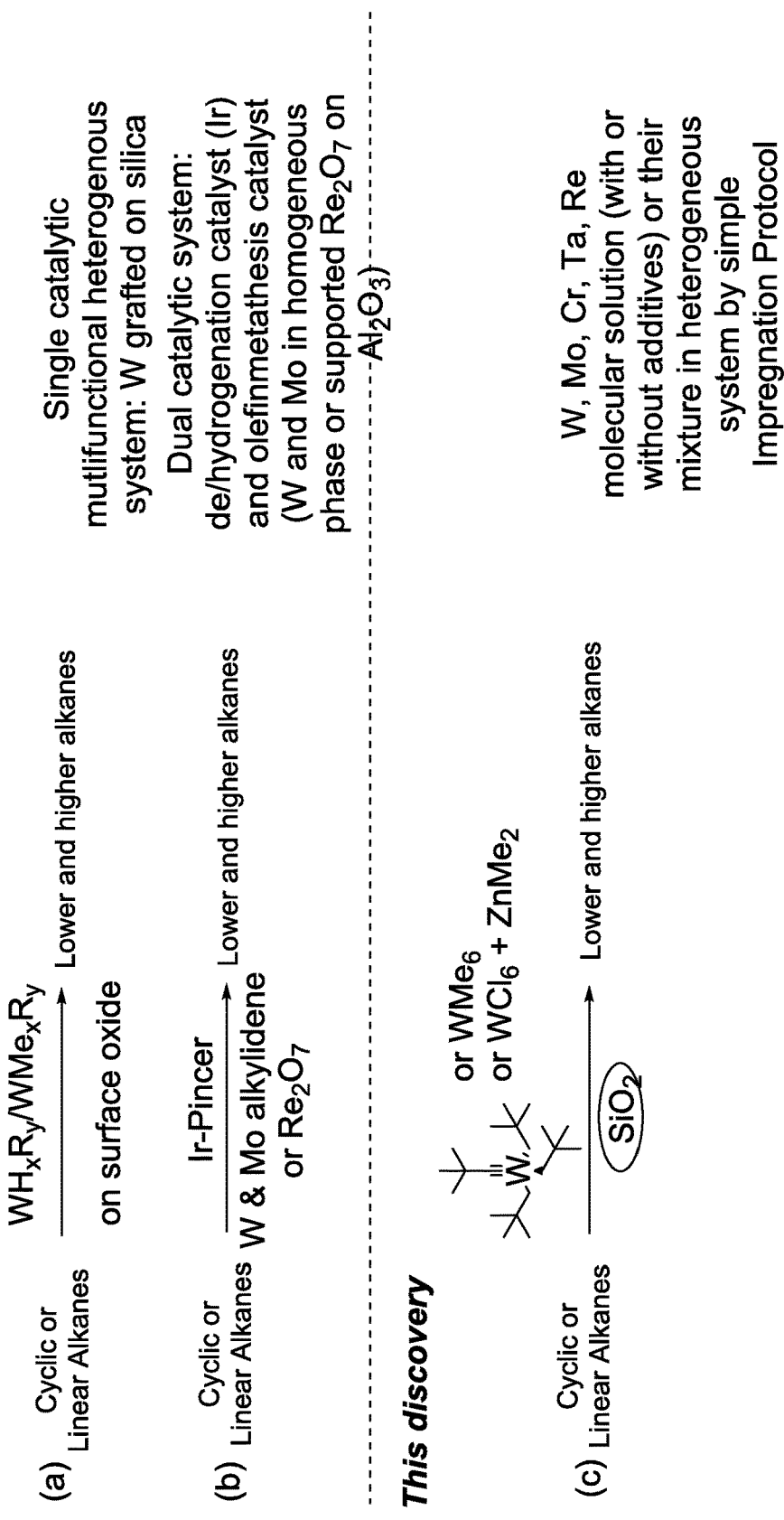
FIG. 1 illustrates the embodiments of the present disclosure as compared to previous methods.

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Embodiments of the present disclosure will employ, unless otherwise indicated, techniques of material science, chemistry, physics, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, dimensions, frequency ranges, applications, or the like, as such can vary. It is also to be understood that the terminology used herein is for purposes of describing particular embodiments only, and is not intended to be limiting. It is also possible in the present disclosure that steps can be executed in different sequence, where this is logically possible. It is also possible that the embodiments of the present disclosure can be applied to additional embodiments involving measurements beyond the examples described herein, which are not intended to be limiting. It is furthermore possible that the embodiments of the present disclosure can be combined or integrated with other measurement techniques beyond the examples described herein, which are not intended to be limiting.

It should be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Discussion:

Embodiments of the present disclosure provide for methods of using a catalytic system to chemically transform a compound (e.g., a hydrocarbon). In an embodiment, the method does not employ grafting the catalyst prior to catalysis. In particular, embodiments of the present disclosure provide for a process of hydrocarbon (e.g., C1 to C20 hydrocarbon) metathesis (e.g., alkane, olefin, or alkyne metathesis) transformation, where the process can be conducted without employing grafting prior to catalysis. Embodiments of the present disclosure may be advantageous over other known methods in that they may have one or more of the following deficiencies: require extreme conditions such as high vacuum conditions and/or temperature conditions, grafting the catalyst to a surface, chemical treatment (e.g., hydrogen), or single site catalytic systems. Embodiments of the method can be used in the chemical industry, petrochemical industry, pharmaceutical industry, polymer industry, material industry.

Embodiments of the present disclosure provide for a method to achieve metathesis (e.g., hydrocarbon metathesis) using an organometallic compound in a reaction solution containing the compound of interest (e.g., a hydrocarbon (e.g., alkane, olefin), fatty acid ester, unsaturated fatty esters, unsaturated fatty acids, and the like) and the addition of a metal oxide (e.g., a silica compound) to form hydrocarbons that are larger or smaller (transforming) than the original hydrocarbon. In an embodiment, the method can be an impregnation protocol that can achieve hydrocarbon metathesis, which includes metathesis of hydrocarbons such as an alkane and a cycloalkane as well as reactions involving hydrocarbons having double bonds or triple bonds (olefins or alkynes).

In an embodiment, the present disclosure includes a process in which it is not necessary to graft an organometallic complex and modify its coordination sphere by an appropriate treatment (e.g., chemical, thermal and/or under hydrogen) before conducting catalysis.

In an embodiment, the process can be applied to olefin metathesis (e.g., the transformation of butenes to propylene). Once the components are mixed with the hydrocarbon, the temperature of the solution is increased to about 25° C. to 250° C., about 25° C. to 150° C. about 100 to 200° C. or to about 200° C.

In an embodiment, the hydrocarbon can include saturated and unsaturated hydrocarbons such as C1-C20 alkanes, C2-C20 alkenes, C2-C20 alkynes, and a mixture thereof, where each can be linear, branched, cyclic, aromatic, or a mixture thereof. In an embodiment, the hydrocarbon can be a C1-C20 hydrocarbon such as ethylene, n-butane, isobutane, butene, decane, cyclooctane, 1-decene, 1-decyne, cyclododecane, hexane, pentanes, $C_6$-$C_{30}$ hydrocarbons (e.g., alkanes, alkenes, alkynes, linear or branch, and/or can be cyclic or include a ring attached to a hydrocarbon chain), or a combination of alfa-olefins and unsaturated fatty acids esters to form diesters, internal olefins and new unsaturated fatty acids esters with a longer hydrophobic portion.

Methods of the present disclosure can be used in redistribution of petroleum components. For example, the method can be used in the transformation of alkanes to gasoline, transformation of ethylene to propylene, transformation of butenes to propylene, cleavage of alkanes by methane, cross metathesis of various alkanes, coupling of aromatics, cross metathesis of various alkanes with aromatics or substituted aromatics, transformation of dinitrogen to ammonia, and the like.

In regard to the pharmaceutical industry, the method can be used in coupling of aromatics by C—C bond formation, metathesis of functionalized paraffins, cross metathesis of functionalized alkanes with alkanes or cycloalkanes, and obtention of cyclic alkanes or functionalized cyclic alkanes.

In regard to the chemical industry, the method can be used in reactions with paraffins, aromatics, or olefins. In particular, the catalytic reaction is active in olefin metathesis, conversion of ethylene or butenes (or their mixture) to propylene, and in the transformation of alkanes like butanes to gasoline.

In an embodiment, the organometallic compound can include Wilkinson $d^0$ $WMe_6$ or Schrock type $d^0$ W metal alkylidyne complex (e.g., $(tBuCH_2)_3W{\equiv}CCMe_3$)) or an organometallic containing an alkyl or several alkyls. In an embodiment, the amount of organometallic compound added to the hydrocarbon can be about 1/10 to 1/100000 mol/mol.

In an embodiment, it is not necessary to introduce the organometallic compound itself but a combination of a precursor inorganic compound and an alkylating agent to the solution containing the hydrocarbon and the metal oxide. In an embodiment, the alkylating agent can include $ZnMe_2$, $SnR_4$ (R=Me, ethyl, propyl, butyl aso), $RAlCl_2$, or AlR$_{3-x}$X$_x$, where R is an hydrocarbyl ligand (e.g., methyl, ethyl, propyl, phenyl, butyl, and the like) X is an halogen, an alkoxide, an aryloxide, and the like. In an embodiment, the amount of the alkylating agent added to the hydrocarbon can be about 1 equivalent per metal atom to 20 equivalents. In an embodiment, the precursor inorganic compound can include the halides alkoxides aryloxides, oxo alkyls, of the transition elements, of the lanthanides, actinides, and the main group elements of the periodical table.

In an embodiment, the metal oxide can include silica, silica-alumina, γ-alumina, zirconia, titania, zinc oxide, magnesia, zeolite, mesoporous zeolite, hybrid organic inorganic material, metal organic framework (MOF), and the like, and a combination thereof. In an embodiment, the metal oxide is partially dehydroxylated. For example, the metal oxide can be pretreated at a temperature of about 200° C. to 700° C. In an embodiment, the silica can be pretreated at room temperature to 700° C. while the silica-alumina, γ-alumina can be pretreated at 500° C. In an embodiment, the amount of the metal oxide added to the hydrocarbon can be about a few percent in weight to 500% in weight.

In an embodiment, once the components are mixed with the hydrocarbon, the mixture can be heated to a temperature of about 25 to 100, about 25 to 200, or to about 200° C. and held at that temperature for about 1 to 30 days, about 3 weeks, about 2 weeks, about 1 week, or about 1 to 3 days. In an embodiment, the mixture can wait for 1 to 30 days before being heated and the results are similar.

In an embodiment, the hydrocarbon (e.g., cyclic and linear alkane) metathesis transformation can be achieved using a fully alkylated inorganic compound (e.g., Schrock type d$^0$ W metal alkylidyne complex impregnated initially on silica). The W organometallic would be immobilized in situ prior the alkane reaction (FIG. 1). This catalytic procedure would be easier to implement than the existing single site metal supported catalytic or dual catalytic systems in an industrial perspective. The catalytic activity of such heterogeneous system with unfunctionalized and functionalized olefins has also been accomplished.

Figure 2:
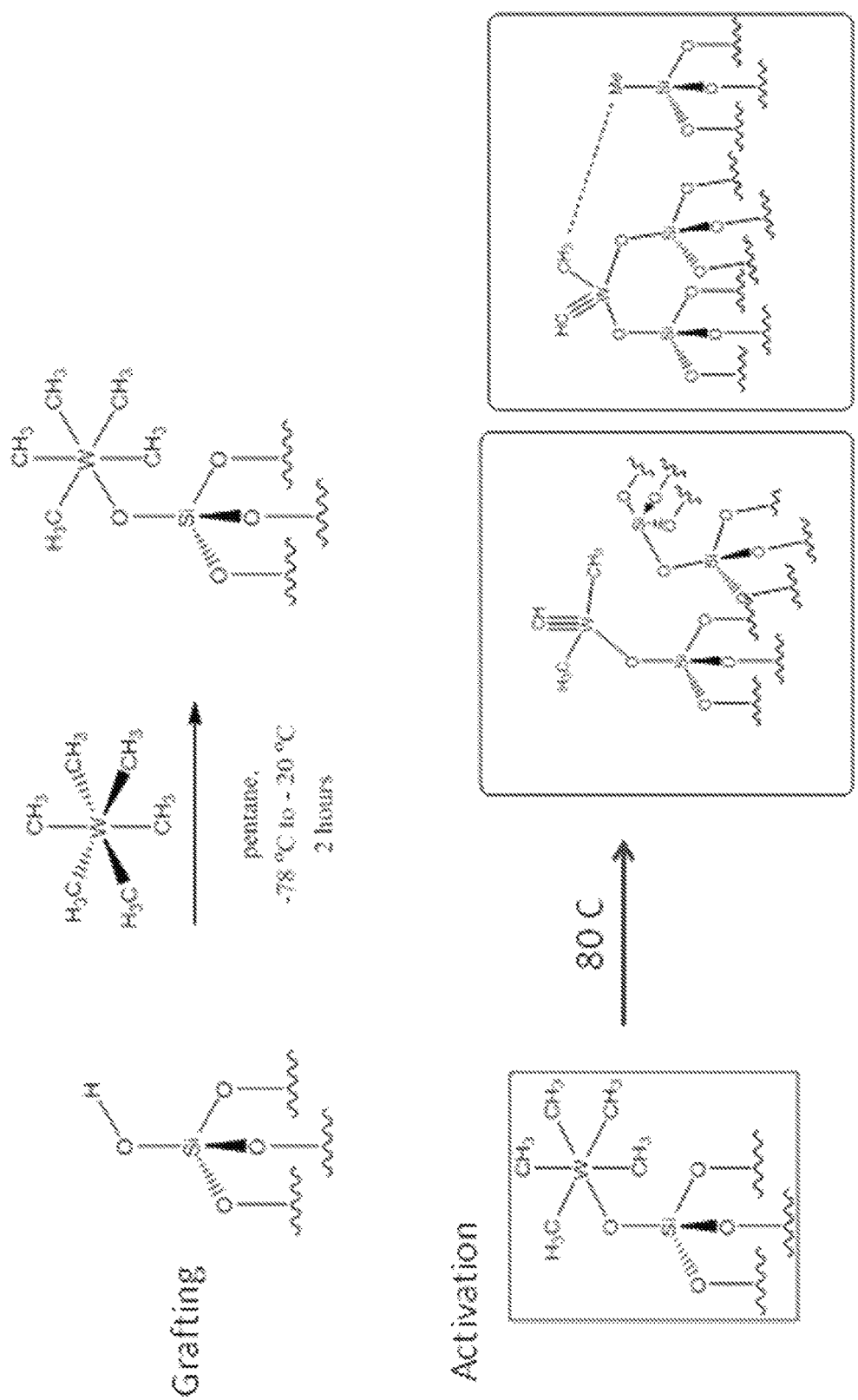
FIG. 2 illustrates the synthesis of silica supported W catalyst via well-defined strategy.

Other methods used in alkane metatheses involving transformation of linear, branched or cyclic hydrocarbons had to include one or more of the following: a) grafting the tungsten alkyl hydride or their mixture to the surface of an oxide (silica, alumina, mesoporous material. Zeolites etc.) under a very high vacuum of 10$^{-5}$ torr; b) treating the grafted species under vacuum thermal (10$^{-5}$ torr) or chemical (Hydrogen) treatment; c) using the grafted complex in the catalytic reaction; d) FIG. 1 and FIG. 2 illustrate the details of the preparation of some alkane metathesis catalysts obtained by grafting an organometallic complex on a surface before obtaining an active metathesis catalyst. (FIG. 2: the first line indicates the grafting and the second line the activation to get activity); e) all the previous strategies were based off of a single site catalytic system where the catalyst was extremely well defined. FIG. 2 illustrates the preparation of the catalysts by successive impregnation and activation for W.

Figure 3A:
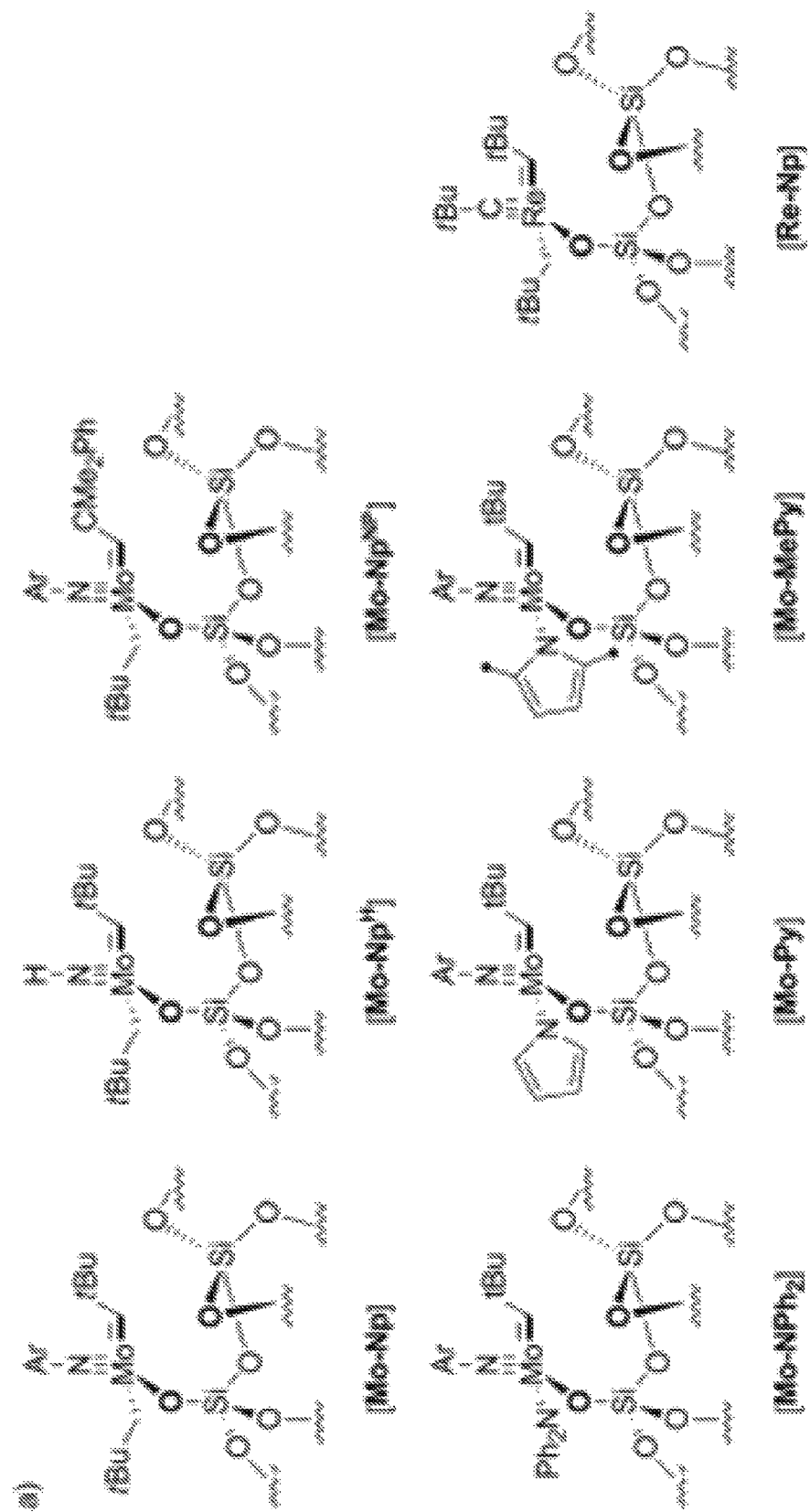
FIGS. 3A-B are alkene metathesis catalyst precursors.
Figure 3B:
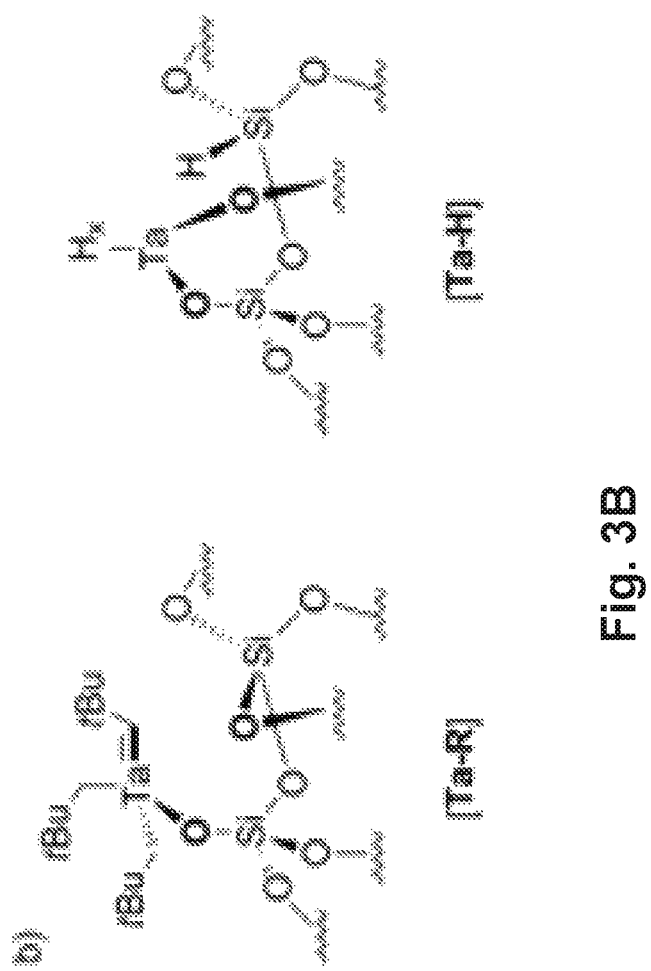

The catalytic procedure of the present disclosure is much easier to implement than the existing well-defined single sites supported catalytic or dual catalytic systems in an industrial perspective. For example silica-supported alkene metathesis catalyst precursors can be used for alkane metathesis as long as the coordination sphere of the metal center contains both alkyl and alkylidene or alkylidyne groups (e.g., (≡SiO)Mo(=NAr)(=CHtBu)(CH$_2$tBu)]) (See FIGS. 3A-B). Other embodiments include: (ArO)$_2$W(=O)(=CHtBu) (ArO=2,6-mesitylphenoxide), [W(=O)(=CHCMe$_2$Ph)(dAdPO)$_2$], containing bulky 2,6-diadamantyl aryloxide ligands, Mo(NAr)(CHCMe$_2$Ph)(dXpz)$_2$, [Mo≡NAr)(=CHCMe$_2$R')(OR)$_2$], [W(=NAr)(=CHtBu)(2,5-Me$_2$NC$_4$H$_2$)$_2$], [(≡SiO)M(ER)(=CHtBu)(R')] (M=Re, Ta, Mo or W; ER=CtBu, NAr or CH$_2$tBu; R'=CH$_2$tBu, NPh$_2$, NC$_4$H$_4$), [Mo(NAr)(CHCMe$_2$R)(CH$_2$tBu)$_2$], 1-R (R=Me or Ph), [(≡SiO)Mo(≡NAr)(=CHCMe$_2$R)(OtBu)], [Mo(≡NAr)(=CHCMe$_2$R$^1$)(NR$_2$)$_2$], [WNAr(CH$_2$tBu)$_2$(CHtBu)] (Ar=2,6-iPrC$_6$H$_3$), W(=O)R$_3$, and the like.

In an embodiment, the present disclosure provides for a straightforward process for hydrocarbon (e.g., cyclic and linear alkanes) metathesis transformation that does not require dedicated tedious grafting process. An embodiment of the present disclosure provides for a precursor complex, (e.g., Wilkinson d$^0$ WMe$_6$ or Schrock type d$^0$ W metal alkylidyne complex) in solution of the hydrocarbon and introduces to this solution a partially dehydroxylated silica (PDS). In an embodiment, the catalytic reaction can be initiated by increasing the temperature of the solution including the components.

Example

Figure 4A:
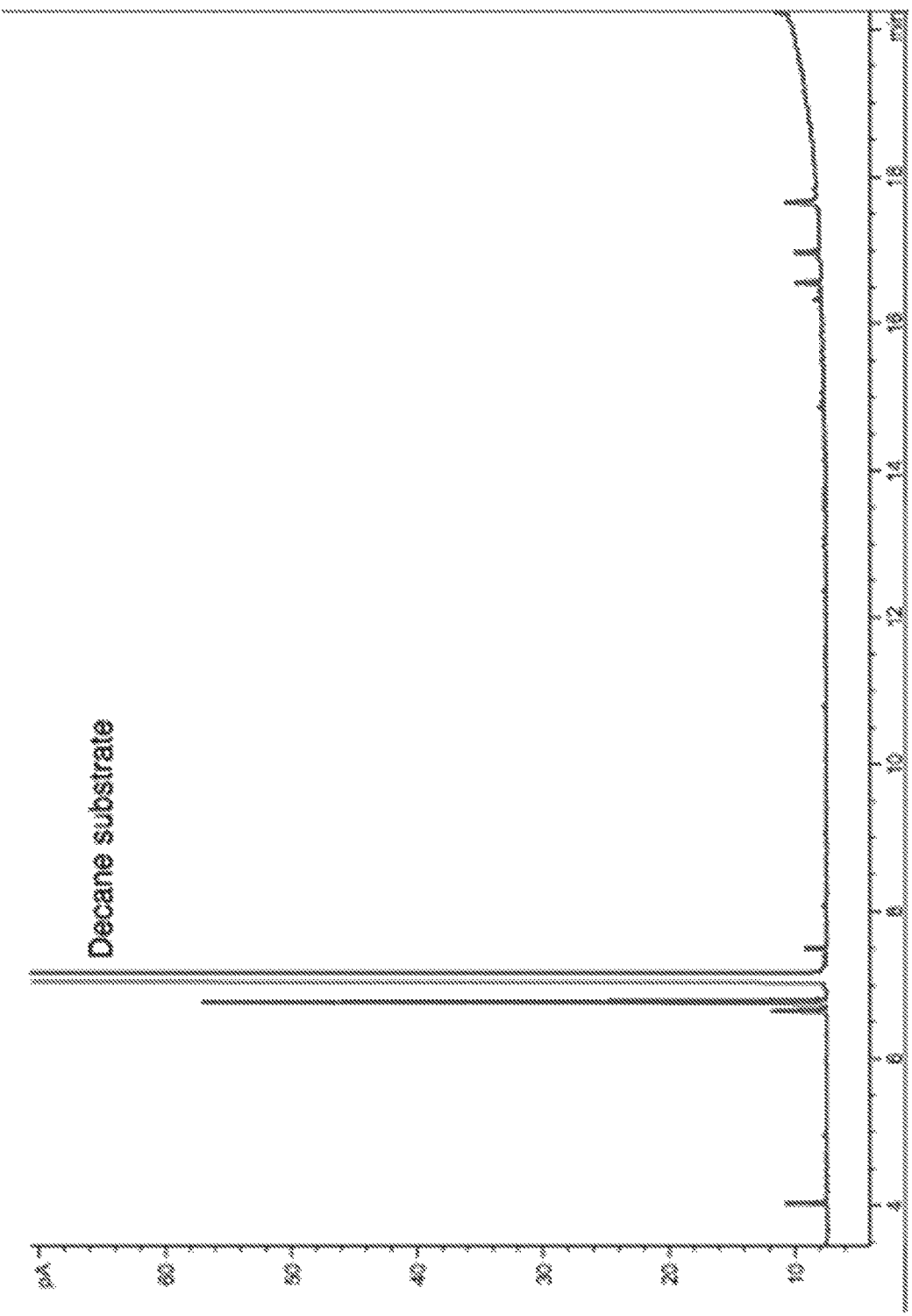
FIGS. 4A and 4B are GC chromatograms of (FIG. 4A) n-decane before reaction and (FIG. 4B) n-decane metathesis products, reaction catalyzed by a molecular solution of [WMe6] in decane (0.98 μmol, 1.97 μmol/mL), n-decane (0.5 mL, mmol), 150° C., 2 days (after addition of silica to the solution).
Figure 4B:
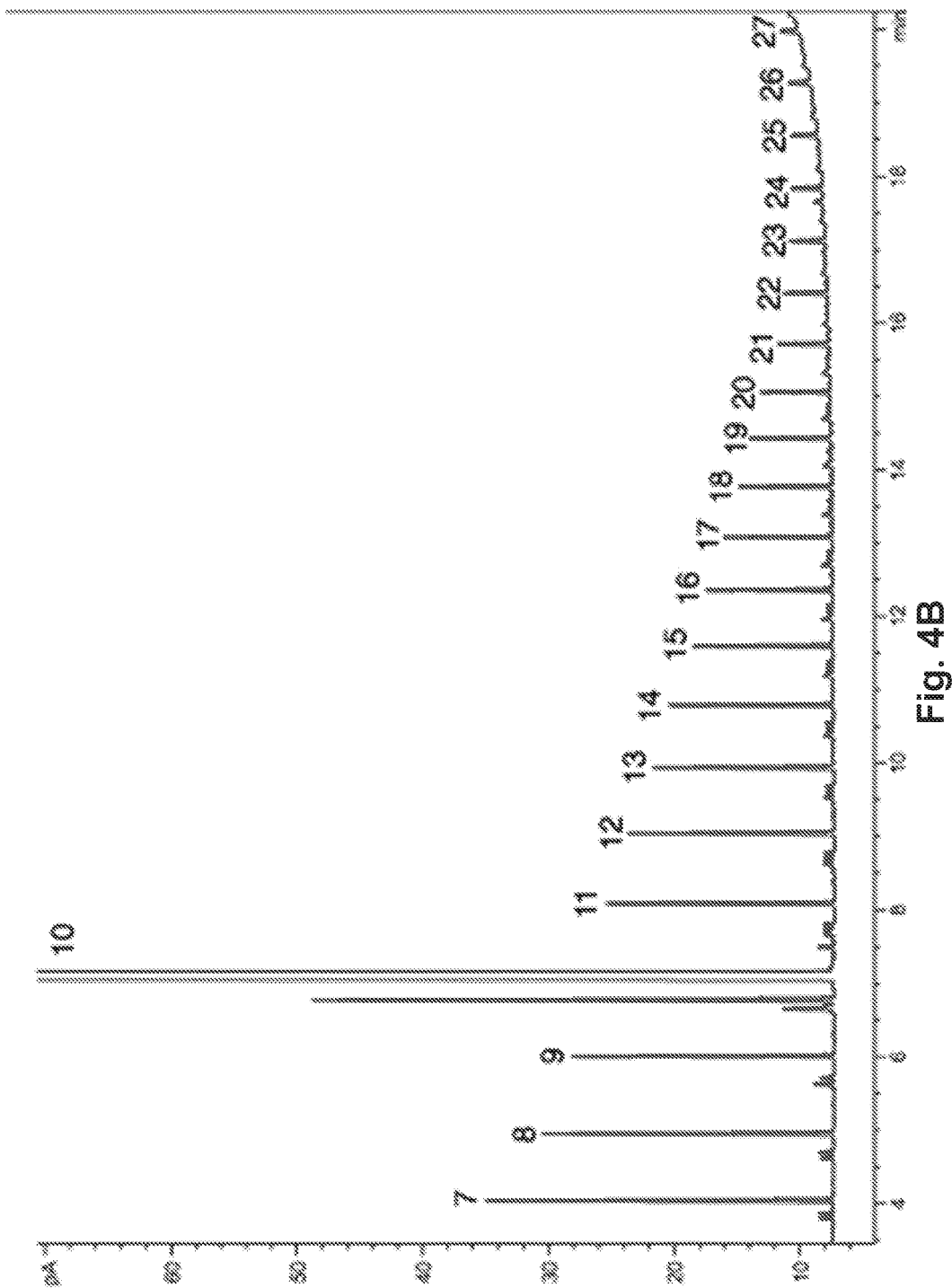

A solution of WMe$_6$ in n-decane, (0.00197 mmol/mL) can be produced following literature procedures.[6] Running the catalytic reaction with exclusively this molecular organometallic solution at 150° C. for 2 days showed no apparent alkane metathesis products. Surprisingly an initial addition of partially dehydroxylated silica (pretreated at 700° C.) (PD Silica$_{(-700)}$) into this organometallic solution under the same reaction conditions led to a mixture of lower and higher alkanes. Moreover, employing a molecular solution of WMe$_6$ in cyclooctane (0.046 mmol/mL) in the presence of an initial amount of PD Silica$_{(-700)}$ produced a distribution of higher molecular weight macrocyclic alkanes along with lower molecular weight cyclic alkanes resulting from ring contraction. In both cases (linear and cyclic alkanes metathesis), the alkane products distribution is similar to the one observed while starting with pre-catalyst 1 (see FIGS. 4A-B for n-decane metathesis).

Figure 5:
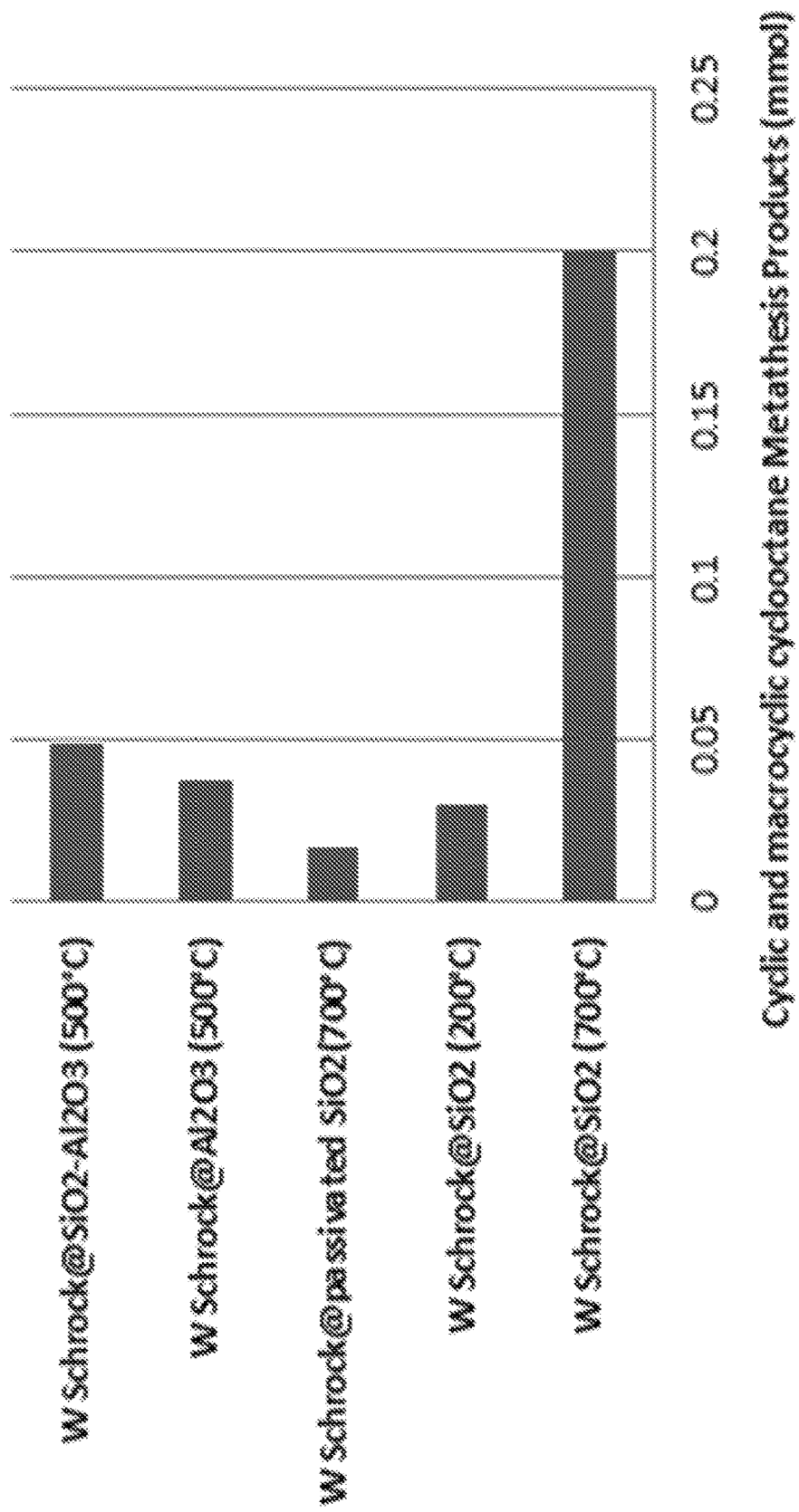
FIG. 5 illustrates cyclooctane metathesis catalyzed by a one-pot procedure with different supports. Reaction conditions: batch reactor, $(tBuCH_2)_3W≡CCMe_3$ (8.9 mg, 19.8 μmol), cyclooctane (0.5 mL, 3.72 mmol) and various surface oxides (50 mg), 72 h, 150° C.
Figure 6:
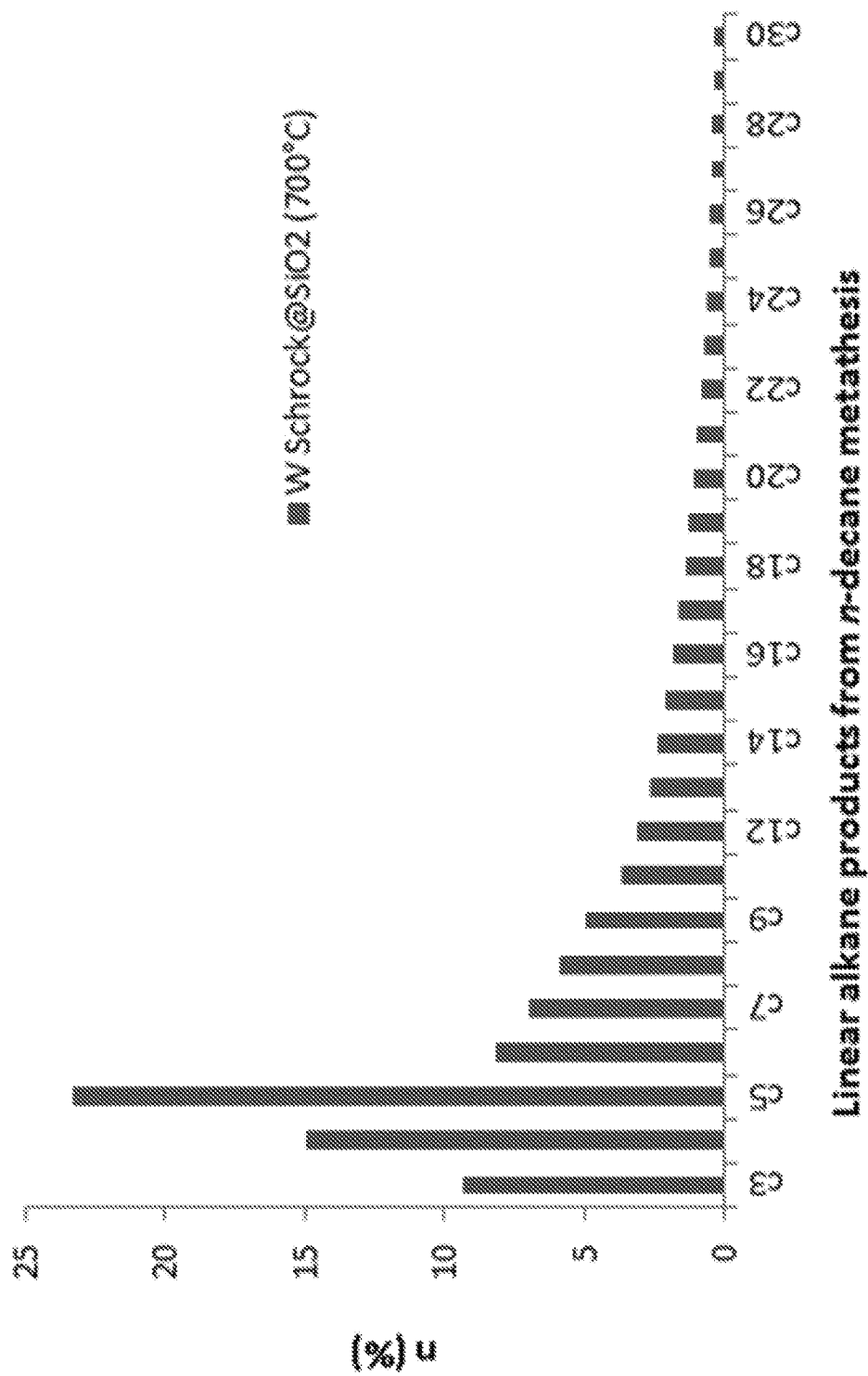
FIG. 6 shows n-decane metathesis products catalyzed by W Schrock©$SiO_2$. Reaction conditions: batch reactor, $(tBuCH_2)_3W≡CCMe_3$ (8.9 mg, 19.8 μmol), n-decane (0.5 mL, 2.57 mmol) and $SiO_2$ (50 mg), 72 h, 150° C.

Substituting PD Silica$_{(-700)}$ with other oxides (50 mg) that were partially dehydroxylated under high vacuum (<10$^{-5}$ mbar) at different temperatures (such as silica pretreated at 200° C., silica-alumina and gamma-alumina pretreated at 500° C.) produce a similar distribution of cyclic alkanes (FIG. 5). In all these catalytic runs, regardless of the nature of the oxide material, cyclooctane was transformed into a mixture of cyclic and macrocyclic alkanes albeit in lower activity than the initial PD Silica$_{(-700)}$ (200° C.) producing a higher amount of cyclic alkane products (1.96 mmol compared to 0.2 mmol) under equal W/alkane molar ratio.

Next, this catalytic procedure was extended to linear alkanes. n-Decane was converted into lower and higher homologues giving a similar distribution to the tandem dual catalytic system using (POCOP)Ir and Mo(Nar)(=CHCMe$_2$Ph)(ORF$_5$)$_2$ complex.[4] These observations are in contrast with the cyclooctane metathesis products in which the two different catalytic systems (single multifunctional and dual catalytic system) differ dramatically. Enhancement activity with this one pot protocol was also observed when the catalytic run is carried out at 200° C. for 3 days.

Figure 7:
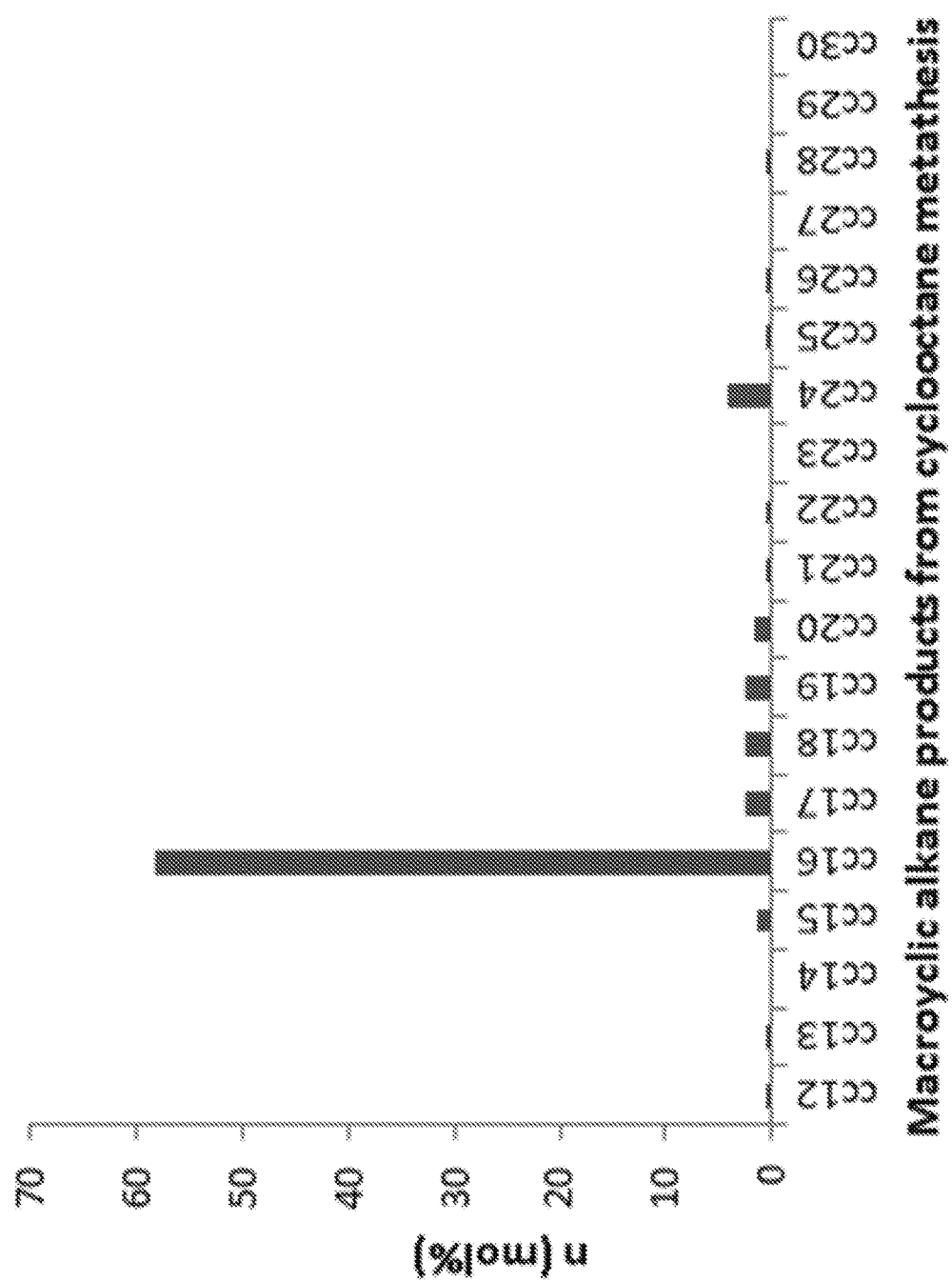
FIG. 7 shows cyclooctane metathesis products catalyzed by W Schrock©$SiO_{2(700)}$. Reaction conditions: batch reactor, $(tBuCH_2)_3W≡CCMe_3$ (300 mg, 667 μmol), cyclooctane (20 mL, 148.8 mmol) and $SiO_{2(700)}$ (2 g), 5 days, 150° C.

To demonstrate the industrial potential of this catalytic procedure, the reaction was scaled by a factor of 40. A solution of (tBuCH$_2$)$_3$W≡CCMe$_3$ (300 mg) in cyclooctane (20 mL) in the presence of PD silica pre-treated at 700° C. (2 g) were stirred and heated at 150° C. for five days. A high selectivity in the formation of the $C_{16}$ cyclohexadecane was observed (>76% of total macrocyclic alkane products). To verify the reproducibility of these results, this catalytic run was repeated twice and gave similar results. This observed high selectivity for cyclohexadecane was attributed to an initial low conversion of cyclooctane. Indeed, previous works on kinetic studies of cyclooctane metathesis revealed that during the initial phase of the process (at low conversion), the dimer and the trimer macrocyclic alkane products are the predominant products (see FIG. 7)[8] Such high selectivity of the dimer ($C_{15}$) was observed at 12 hours when running a catalytic run of cyclooctane (0.5 mL) catalyzed by [≡Si—O—WMe$_5$] 1.

Figure 8:
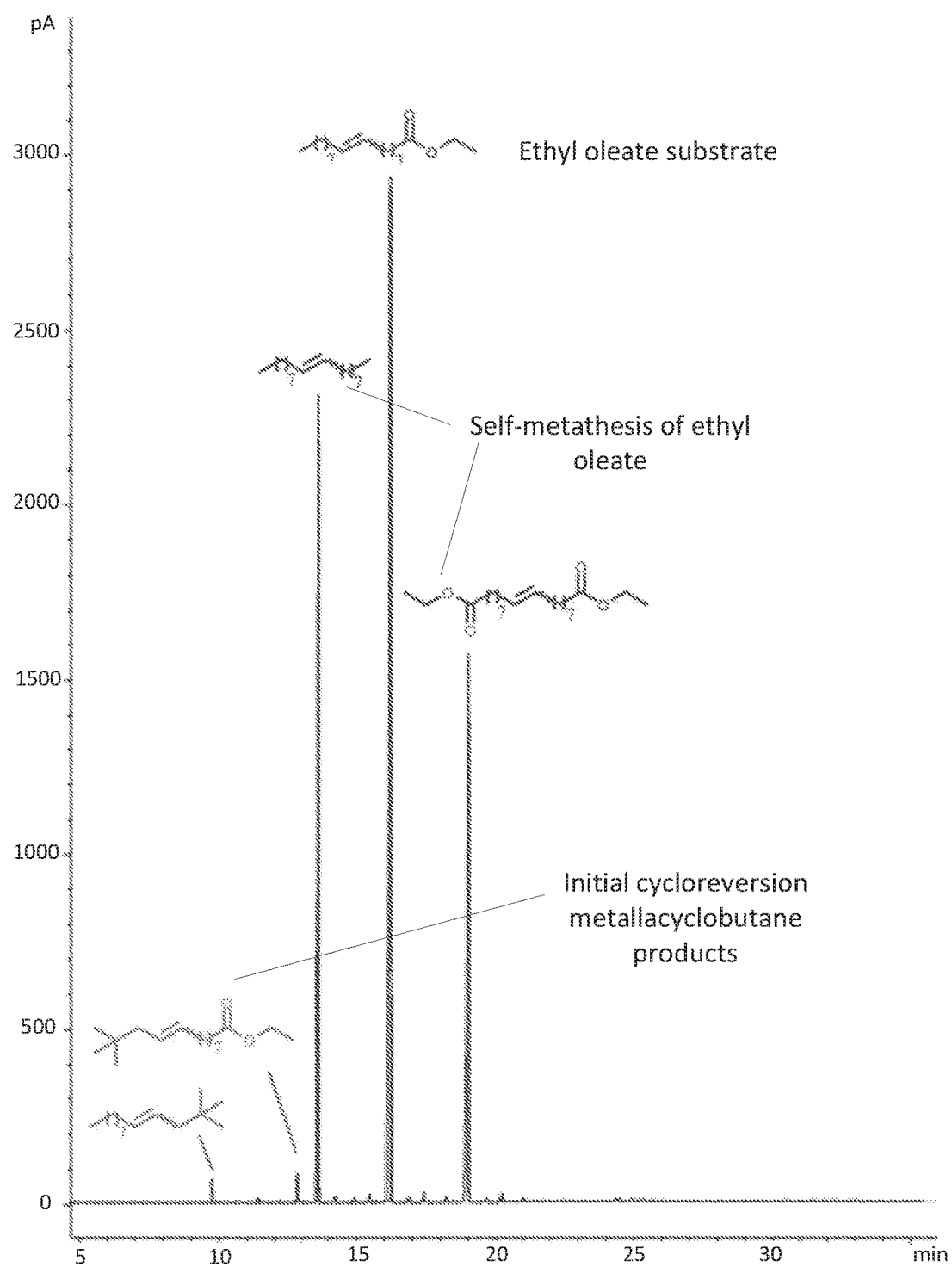
FIG. 8 shows ethyl oleate metathesis products catalyzed by W Schrock©$SiO_2$. Reaction conditions: batch reactor, $(tBuCH_2)_3W≡CCMe_3$ (7 mg, 19.8 μmol), ethyl oleate (0.5 mL, 3.72 mmol), $SiO_2$ (100 mg), 3 h, 150° C.

Finally, it was found that this one pot protocol with Schrock type d⁰ W metal alkylidyne complex is also active for the olefin metathesis. Indeed, 1-decene was converted into an equilibrium mixture of $C_2$-$C_{30}$ terminal and internal olefins by successive isomerization and olefin metathesis (ISOMET). 2 catalyzes also the ISOMET reaction of 1-decene (FIG. 8).

This one pot protocol was also efficient in converting unsaturated fatty acid ester (FAE) into the corresponding diesters. For instance, ethyl undecylenate and ethyl oleate produced the corresponding self-metathesis products. Interestingly, for ethyl oleate, the initial products of the cross metathesis between the neopentylidene W ligands and FAE, tertbutyl olefins were observed (in green). Yet again, the formation of these olefins strongly supports the formation of W bis-carbene intermediate species from a silica supported W alkyl/alkylidyne species.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

We claim at least the following:

1. A method of hydrocarbon metathesis, comprising:
   contacting a partially dehydroxylated metal oxide with a molecular solution including an organometallic compound and one or more hydrocarbons to form a mixture; and
   heating that mixture to or at a temperature of at least about 100° C. sufficient to generate a catalyst in situ and achieve hydrocarbon metathesis in a one-pot protocol.

2. The method of claim 1, wherein the hydrocarbon is selected from the group consisting of a saturated hydrocarbon, a unsaturated fatty acid ester, an olefin, a functionalized olefin, and a combination thereof.

3. The method of claim 1, wherein the organometallic compound is selected from: Wilkinson d⁰ WMe$_6$ or Schrock type d⁰ W metal alkylidyne complex.

4. The method of claim 1, wherein the metal in the organometallic compound is a transition metal or mixture thereof.

5. The method of claim 4, wherein the transition metal is selected from the group consisting of: Ti, Zr, Hf, Ta, Nb, V, Cr, Mo, W, Re, and their mixtures.

6. The method of claim 1, wherein the organometallic compound containing a chloride or an aryl oxide is associated with an alkylating agent.

7. The method of claim 6, wherein the alkylating agent is MeLi or Me$_2$Zn.

8. The method of claim 1, wherein the metal oxide is selected from the group consisting of: silica, silica-alumina, γ-alumina, mesoporous silica, zeolite, metal organic frameworks (MOF), organic-inorganic mixed oxides, carbon black, carbon nanotubes, and a combination thereof.

9. The method of claim 1, wherein the hydrocarbon is an alkane and the method forms gasoline from the transformation of the alkane.

10. The method of claim 1, wherein the hydrocarbon is ethylene and the method forms propylene from the transformation of ethylene.

11. The method of claim 1, wherein the hydrocarbon is butene and the method forms propylene from the transformation of butene.

12. The method of claim 1, wherein the hydrocarbon is a saturated or unsaturated C1-C20 hydrocarbon.

13. The method of claim 1, wherein the hydrocarbon is selected from a group consisting of: a C1-C20 alkane, a C2-C20 alkene, a C2-C20 alkyne, and a combination thereof, wherein each hydrocarbon is linear, branched, cyclic, and/or aromatic.

14. The method of claim 1, wherein the hydrocarbon is selected from a group consisting of: ethylene, n-butane, isobutane, butene, decane, cyclooctane, cyclododecane, hexane, pentanes $C_6$-$C_{30}$ hydrocarbons, 1-decene, 1-decyne, and a combination thereof.

15. The method of claim 1, wherein the hydrocarbon metathesis does not employ grafting prior to catalysis.

16. The method of claim 1, wherein contacting includes heating the mixture to a temperature ranging from about 25° C. to about 200° C.

17. A method of hydrocarbon metathesis, comprising:
   contacting one or more of a precursor inorganic compound, an alkylating agent, a metal oxide, and one or more hydrocarbons to form a mixture; and
   heating that mixture to or at a temperature of at least about 100° C. sufficient to generate a catalyst in situ and achieve hydrocarbon metathesis in a one-pot protocol.

18. The method of claim 17, wherein the alkylating agent is one or more of ZnMe$_2$, SnR$_4$, RAlCl$_2$, and AlR$_{3-x}$X$_x$, where R is a hydrocarbyl ligand and X is one or more of a halogen, alkoxide, and aryloxide.

19. The method of claim 17, wherein the precursor inorganic compound is one or more of a halide, alkoxide, aryloxide, and oxoalkyl of one or more transition metals, lanthanides, and actinides.

* * * * *